(12) United States Patent
Hosoi et al.

(10) Patent No.: US 9,556,343 B2
(45) Date of Patent: Jan. 31, 2017

(54) CONDUCTIVE FINE PARTICLE AND METAL PASTE FOR ELECTRODE FORMATION AND ELECTRODE

(71) Applicant: TANAKA KIKINZOKU KOGYO K.K., Tokyo (JP)

(72) Inventors: Takuya Hosoi, Kanagawa (JP); Nobuhisa Okamoto, Kanagawa (JP); Koichi Sakairi, Kanagawa (JP)

(73) Assignee: Tanaka Kikinzoku Kogyo K. K., Tokyo (JP)

( * ) Notice: Subject to any disclaimer, the term of this patent is extended or adjusted under 35 U.S.C. 154(b) by 35 days.

(21) Appl. No.: 14/252,762

(22) Filed: Apr. 14, 2014

(65) Prior Publication Data
US 2015/0123045 A1 May 7, 2015

Related U.S. Application Data

(62) Division of application No. 13/387,976, filed as application No. PCT/JP2011/065673 on Jul. 8, 2011, now Pat. No. 8,771,553.

(51) Int. Cl.
*H01B 1/22* (2006.01)
*C09D 5/24* (2006.01)
(Continued)

(52) U.S. Cl.
CPC ............. *C09D 5/24* (2013.01); *G01N 27/4075* (2013.01); *H01B 1/02* (2013.01); *H01B 1/22* (2013.01); *Y10T 428/2991* (2015.01)

(58) Field of Classification Search
CPC ................ H01B 1/00; H01B 1/22; H01B 5/00
See application file for complete search history.

(56) References Cited

U.S. PATENT DOCUMENTS 5,126,915 A 6/1992 Pepin et al.
6,265,090 B1 7/2001 Nishide et al.
(Continued)

FOREIGN PATENT DOCUMENTS

JP 10026603 A 1/1998
JP 2000-160268 A 6/2000
(Continued)

OTHER PUBLICATIONS

Chadhuri et al "Core/Shell Nanoparticles: Classes, Properties, Synthesis Mechanisms, Characterization, and Applications", Chem Rev 2012, 112, 2373-2433.
(Continued)

*Primary Examiner* — Mark Kopec
(74) *Attorney, Agent, or Firm* — Roberts & Roberts, LLP

(57) ABSTRACT

An object of the present invention is to provide a conductive fine particle for producing a metal paste that can produce an electrode film having a low resistance, and a metal paste utilizing the conductive fine particle. The present invention is a conductive particle for electrode formation having a core/shell structure, and the conductive particle comprises a core particle made of Pt or a Pt alloy and having a particle diameter of 10 to 200 nm, and a shell made of a ceramic containing $Al_2O_3$ or $ZrO_2$ and covers at least a part of the core particle, wherein the ceramic constituting the shell is added in an amount of 0.5 to 15% by weight based on the core particle to cover the core. The core particle is preferably Pt or a Pt alloy alloyed with Pd, Au, Ag, or Rh.

7 Claims, 2 Drawing Sheets

(51) Int. Cl.
*H01B 1/02* (2006.01)
*G01N 27/407* (2006.01)

(56) References Cited

U.S. PATENT DOCUMENTS

| | | | |
|---|---|---|---|
| 7,820,291 B2 | 10/2010 | Kim et al. | |
| 8,771,553 B2 * | 7/2014 | Hosoi | H01B 1/02 252/514 |
| 2003/0152863 A1 | 8/2003 | De La Prieta et al. | |
| 2007/0092987 A1 | 4/2007 | Kim | |
| 2011/0250122 A1 | 10/2011 | Joo et al. | |
| 2011/0311635 A1 | 12/2011 | Stucky et al. | |

FOREIGN PATENT DOCUMENTS

| | | |
|---|---|---|
| JP | 2003-531456 A | 10/2003 |
| JP | 03-510050 B2 | 3/2004 |
| WO | 2004066319 A1 | 8/2004 |

OTHER PUBLICATIONS

Secco et al "Tailoring sphere density for high pressure physical property measurements on liquids", Rev Scientific Instruments 72.4, Apr. 2001, pp. 2114-2116.

* cited by examiner

Example 1

Fig. 2B Conventional Example 1

CONDUCTIVE FINE PARTICLE AND METAL PASTE FOR ELECTRODE FORMATION AND ELECTRODE

CROSS REFERENCE TO RELATED APPLICATION

This application is a division of U.S. patent application Ser. No. 13/387,976 filed Jan. 30, 2012, now U.S. Pat. No. 8,771,553, which was a U.S. National Phase entry of international patent application PCT/JP2011/065673 having international filing date of Jul. 8, 2011, which application claims foreign priority to Japanese patent application 2010157801 filed Jul. 12, 2010.

FIELD OF THE INVENTION

The present invention relates to a conductive fine particle for forming various electrodes such as a sensor electrode, a heater electrode, and a lead electrode, and further relates to a metal paste for electrode formation using the conductive fine particle.

BACKGROUND OF THE INVENTION

In producing a sensor electrode, a heater electrode and the like for various gas sensors such as an oxygen sensor, a NOx sensor, and an exhaust temperature sensor, these electrodes are generally produced by coating a metal paste including a conductive metal powder on a substrate by various methods such as a screen printing method and calcining it. The reasons for frequently using a form of a metal paste are that the metal paste can be adapted to a complex electrode pattern, and furthermore that coating and calcining the metal paste on a green sheet forming a ceramic substrate allow a substrate and an electrode to be produced simultaneously, which is preferable from the viewpoint of production efficiency.

A metal paste for electrode formation, which has been conventionally used is one that is obtained by mixing a conductive particle such as a precious metal and a ceramic powder such as $Al_2O_3$ or $ZrO_2$ (YSZ) with a solvent. The reason for mixing a ceramic powder in a metal paste is that when the metal paste is coated on a green sheet and calcined to produce a substrate and an electrode as described above, the difference in shrinkage rate between the metal paste and the green sheet is so modified as to solve problems for warpage and deformation of a substrate due to the difference in shrinkage rate, thereby improving adhesion of an electrode. In addition, there is also an advantage that the mixing of a ceramic in a metal paste could prevent a conductive particle from being excessively sintered upon calcining.

On the other hand, since a metal paste for electrode formation is a precursor material for an electrode, it is naturally required to be low in electric resistance value (specific resistance). However, the mixing of a ceramic powder is an obstructive factor in terms of lowering the resistance of an electrode, and there has been a tendency that the resistance value of an electrode film formed by calcining a metal paste would be significantly higher than that of a bulk metal. That is, although the improving of adhesion with mixing a ceramic in a metal paste is contrary to a demand of lowering the resistance of an electrode, no or quite a little ceramic to be mixed makes an electrode formation itself become impossible.

PRIOR ART DOCUMENTS

Patent Literature

Patent Literature 1: Japanese Patent No. 3510050

SUMMARY OF THE INVENTION

Problems to be Solved by the Invention

The present invention has been made with attention focused on the above-mentioned problem, and an object of the present invention is to provide a conductive fine particle for producing a metal paste that can produce an electrode film having a low resistance, and a metal paste utilizing the conductive fine particle.

Means for Solving the Problems

The present inventors made various studies on the problem, and firstly discussed a factor of a high resistance value of an electrode film formed with a conventional metal paste. The conventional metal paste in a state where a conductive particle and a ceramic particle are dispersed in a solvent is calcined so that the conductive particle is sintered and bound, and thus allowed to be conductive as an electrode, but the ceramic powder is also caused to be sintered upon calcining the metal paste. In this case, since there is a difference in temperature between the temperature of sintering the conductive particle (metal) and that of sintering the ceramic powder, and the temperature of sintering the conductive particle is lower, the conductive particle is preferentially sintered in the process of calcining. An unsintered ceramic particle present around the conductive particle aggregates in such a manner as to be pushed from the conductive particle that has already started to be sintered. Then, the sintering of the ceramic progresses in a state where the conductive particle and the ceramic particle are nonuniformly dispersed, thereby generating a coarse ceramic particle. The present inventors considered that the high resistance in the prior art is due to such a coarse ceramic powder sintered that affects the resistance of an electrode.

On the other hand, the ceramic powder is essential for electrode formation, as described above, and thus the removal of the ceramic powder from the metal paste is not a preferable solution. Accordingly, the present inventors made studies so as to discover a metal paste having a fine ceramic particle that can be dispersed therein in the process of calcining. As a result, they found that preferred is a conductive particle having a core/shell structure where the conductive particle is covered with a ceramic.

The invention of the present application for solving the problem is a conductive particle for electrode formation having a core/shell structure, the conductive particle comprising a core particle that is made of Pt or a Pt alloy and has a particle diameter of 10 to 200 nm, and a shell that is made of a ceramic containing $Al_2O_3$ or $ZrO_2$ and covers at least a part of the core particle, wherein the ceramic constituting the shell is added in an amount of 0.5 to 15% by weight based on the core particle to cover the core.

The conventional metal paste has been one obtained by separately dispersing a conductive particle and a ceramic powder in a solvent. The invention of the present application is a metal paste obtained by binding a conductive particle and a ceramic powder in the runup to pasting to form a core/shell structure, and dispersing it in a solvent. The conductive particle is thus allowed to have a core/shell structure to make the ceramic powder fine so as to decrease a lag between the time of starting the sintering of the conductive particle and that of the ceramic powder. That is, when a paste with the conductive particle having a core/shell structure is calcined, a shell (ceramic) is caused to be detached from a core particle before the core particle is sintered. The temperature of the ceramic detachment is relatively high and is close to the temperature of the ceramic sintering. Therefore, the conductive particle cannot be sintered while the core particle is covered with the shell, and starts to be sintered at a stage at which the shell has been detached. However, the ceramic also starts to be sintered at the stage, and thus the uniform dispersion state can be maintained.

In the present invention, the conductive particle is made fine, and thus the ceramic covering the conductive particle is also made fine. The fine ceramic in a uniform dispersion state as described above can be prevented from being coarsened as found in the conventional case even when being sintered. The present invention is thus aimed to refine a ceramic particle in an electrode and to make its resistance low by making the conductive particle fine and applying a core/shell structure.

Hereinafter, the present invention will be described. In the conductive particle according to the present application, the core particle is made of Pt or a Pt alloy. These metals are favorable in conductivity, and also excellent in heat resistance. Since some of various sensors such as an exhaust sensor for an automobile may be used under high temperature, these metals are suitable for an electrode material for such sensors.

Which one of Pt and a Pt alloy is used as the core particle can be selected depending on the use and the demanded characteristics. Pt is lower in resistance than a Pt alloy, and suitable for the use such as a sensor electrode and a lead electrode which primarily require for making a resistance low.

On the other hand, although a Pt alloy is rather higher in resistance than Pt, it is low in temperature coefficient of resistance (TCR) and thus suitable for the use such as a heater electrode. Here, Pd, Au, Ag and Rh are preferable as a metal alloyed with Pt for a Pt alloy. In addition, a Pt—Pd alloy including Pd is preferable in that it has good compatibility with a ceramic serving as a substrate and that it also shows good wettability when being converted into a paste. Here, it is to be noted that a Pt—Pd-alloy preferably contains 30% by weight or less of Pd. The reason for this is that if the content of Pd is too high, a Pd oxide is likely deposited in the process of calcining, thereby decreasing the reliability of an electrode.

Pt or a Pt alloy being the core particle may further include 3% by weight or less of Al or Zr. Such Al or Zr, which is a component of the core particle, is included while being diffused in the core particle when the core particle is covered with the ceramic in a method of producing a conductive particle as described later. Al or Zr in the core particle is released from the core particle and oxidized upon calcining the metal paste to be finely dispersed like the shell as the ceramic in an electrode film. Therefore, there is no problem if the core particle is an alloy containing Al or Zr, and the core particle does not always have to contain Al or Zr.

The shell covering the core particle is made of a ceramic of $Al_2O_3$ or $ZrC_2$ in consideration of bondability to a ceramic substrate. It is preferable if this ceramic shell covers the core particle uniformly, however it is acceptable if the entire surfaces of all of the conductive particles are not covered. For example, it is permissible if a conductive particle having a ceramic partially bonded with a core particle is included. In this case, when using, as a measure of an amount of the ceramic shell, the ratio of the amount to an amount of the conductive particle in terms of weight, the amount of the ceramic needs to be 0.5 to 15% by weight based on the core particle. The reason for this is that if the amount exceeds 15% by weight, the resistance value will be excessive when an electrode is formed. In addition, if the amount of the ceramic is less than 0.5% by weight, peeling, warpage and deformation are likely caused when the paste is formed, and coated and calcined. The amount of the ceramic is more preferably 1 to 15% by weight. It is to be noted that the thickness of the ceramic shell preferably ranges from 1 to 100 nm. In addition, $ZrO_2$ includes a stabilized zirconia such as YSZ and a partially-stabilized zirconia such as P—YSZ.

A method of producing the conductive particle having a core/shell structure as described above includes a method utilizing a gas phase reaction in a high temperature atmosphere. This method is as follows: a powder of a metal/alloy being the core particle and a ceramic powder being the shell are mixed, the mixed powders are released in a higher temperature atmosphere than boiling points of both the components and cooled, and the resulting fine particle is recovered. In this case, the higher temperature atmosphere where a powder being a raw material is released is preferably a plasma atmosphere.

With respect to the conductive particle having a core/shell structure produced as described above, a particle size of the core particle can be adjusted by heat treatment. This heat treatment (granulation treatment) can enlarge the size of the core particle to 200 nm.

A metal paste with the conductive particle according to the present invention applied is one obtained by mixing this conductive particle and a solvent. A solvent applicable to the metal paste includes common solvents such as ethylene glycol, propylene glycol, ethyl cellosolve, butyl cellosolve, ethylene glycol monophenyl ether, ethylene glycol monomethyl ether acetate, benzyl alcohol, kerosene, paraffin, toluene, cyclohexanone, y-butyrolactone, methyl ethyl ketone, N-methyl pyrrolidone, N-dimethyl formamide, N-methyl acetamide, N,N-dimethyl acetamide, butyl carbitol, turpentine oil, a-terpineol, and terpineol. In particular, something like α-terpineol is suitable.

An amount of the conductive particle mixed is preferably 50 to 90% by weight based on the entire paste. The reason for this is that if the amount is less than 50% by weight, an electrode film becomes too thin, and if the amount exceeds 90% by weight, it makes it difficult to prepare a paste.

In addition, a resin usually used may be added to the metal paste in order to allow the metal paste to have viscosity and thixotropy. This resin is generally a natural resin, an amino-based resin, or an alkyd resin. In particular, something like ethyl cellulose is suitable.

When an electrode is produced with this paste for electrode formation, the calcining temperature is preferably 1300 to 1600° C. The reason for this is that the paste can be sufficiently sintered to obtain an electrode having a low resistance value. In the electrode film thus formed, a fine ceramic particle ($Al_2O_3$ particle, $ZrO_2$ particle) is uniformly dispersed and specifically the size of not less than half of the ceramic particle is 300 nm or less.

Advantageous Effects of Invention

As described above, the conductive particle according to the present invention is applied to a metal paste, and calcining the metal paste enables formation of an electrode film having a low resistance where a fine ceramic particle is dispersed. By making it possible to form an electrode film having a low resistance, the thickness of the electrode film is allowed to be thin, thereby leading to reduce the amount of a precious metal such as Pt to be used and lower the cost of an apparatus.

BRIEF DESCRIPTION OF THE DRAWINGS

FIG. 2A and FIG. 2B show cross-sectional photographs of electrodes produced in Example 1 and Conventional Example 1.

DETAILED DESCRIPTION OF THE PREFERRED EMBODIMENTS

First Embodiment: Hereinafter, embodiments of the present invention will be described. In the present embodiment, a conductive particle covered with $Al_2O_3$ having a core particle made of each of Pt and a Pt—Pd alloy was produced to make a metal paste, and an electrode obtained by calcining the metal paste was evaluated for a resistance value thereof. In addition, with respect to the core particle made of a Pt—Pd alloy, characteristics of a paste associated with the variation of the content of Pd were evaluated.

(i) Production of Conductive Particle

A Pt powder having an average particle size of 10 nm and an $Al_2O_3$ powder having an average particle size of 10 nm were mixed with a V-shaped mixer to prepare uniform mixed powders. The mixing ratio in this case corresponds to an amount of an $Al_2O_3$ shell added. The mixed powders were released in a plasma atmosphere under an argon atmosphere in a high frequency induction thermal plasma apparatus. The generated fine powders were recovered by a filter. The foregoing step led to obtain conductive particle powders of a core/shell structure with Pt as a core particle (Examples 1 and 2). The particle dimension (maximum dimension) of the conductive particle powder was read from a TEM image, and the particle sizes of the core particle and the entire were 20 nm and 40 nm, respectively.

Figure 1A:
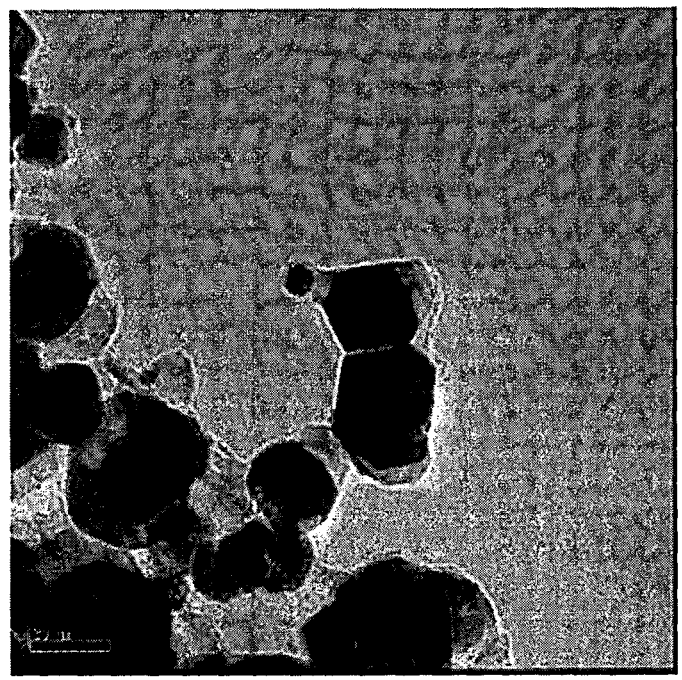
FIG. 1A and FIG. 1B show TEM images of conductive particles (Pt/$Al_2O_3$) produced in the present embodiment.
Figure 1B:
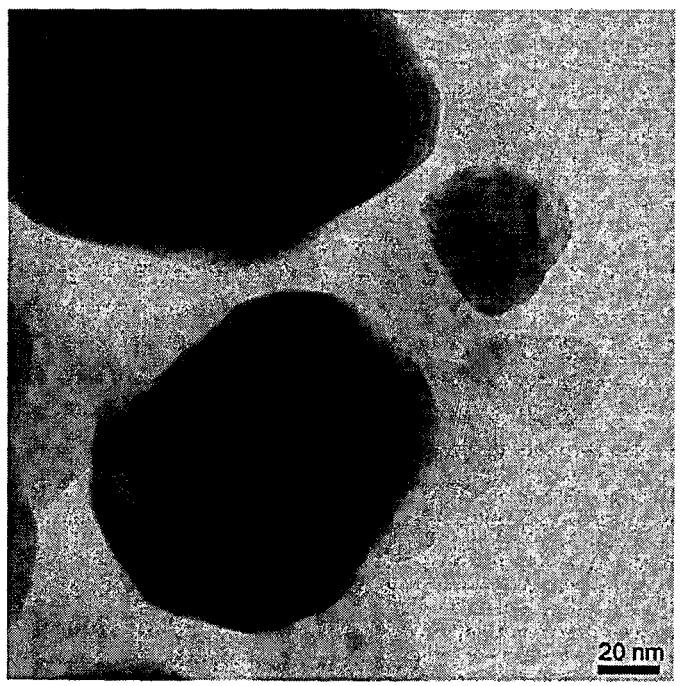

FIG. 1($a$) shows a TEM image of the produced conductive particle powder of a core/shell structure. The composition analysis for this conductive particle powder was conducted with an EDX analysis, and it has been confirmed that the conductive particle powder includes 0.93% by weight of Al. This Al is considered to be from Al of the $Al_2O_3$ powder diffused in a Pt particle released in a plasma atmosphere in the production step.

Conductive particles in which a Pt—Pd alloy (Pd 25% by weight) was applied as a core particle were also produced in the same manner as described above (Examples 3 and 4). As raw material powders, a Pt particle having an average particle size of 10 nm, an $Al_2O_3$ powder having an average particle size of 10 nm, and a Pd powder having an average particle size of 40 nm were used. Other production conditions were the same as described above. The particle size of the core particle was 20 nm in this case.

Conductive particles, in which a Pt—Pd alloy was applied as a core particle, produced in the same manner as in Examples 3 and 4 described above were heat-treated at 900° C. for 1 hour, and granulated (particle-size adjusted) to produce conductive particles (Examples 5 and 6). The particle size of the core particle was 200 nm in this case. FIG. 1($b$) shows a TEM image of the produced conductive particle powder of a core/shell structure.

As comparison with the powder of a core/shell structure in each of the Examples, fine particles made of each of Pt and a Pt—Pd alloy, without being covered with $Al_2O_3$, were also produced (Comparative Examples 1 to 4). These fine particles were produced by releasing a Pt powder and a Pd powder as raw materials in a plasma gas phase.

(ii) Preparation of Paste for Electrode Formation

Each of the conductive particles produced above was placed in ester alcohol as an organic solvent, further mixed with a diamine-based surfactant and ethyl cellulose, and mixed and kneaded in a three-roll mill to form a paste. An amount of the conductive particle mixed was 70% by weight. In addition, in this paste preparation, as conventional metal pastes, there were prepared those obtained by mixing a metal powder with a particle size of 0.7 µm and an $Al_2O_3$ powder having a particle size of 0.3 µm (Conventional Examples 1 to 4). Furthermore, with respect to the particle having a particle size of 20 nm only made of a core particle without being covered with $Al_2O_3$ (Comparative Examples 1 to 4), an $Al_2O_3$ powder having a particle size of 10 nm was mixed with a conductive particle to form a metal paste.

(iii) Preparation of Electrode

Each of the metal pastes described above was coated on a 96% alumina substrate with a screen printing and formed. Thereafter, the resultant was dried at 120° C. for 10 minutes and subjected to calcination treatment at 1500° C. for 1 hour to prepare an electrode film.

The resistance value for the electrode film produced in the foregoing step was measured using a digital multi-meter by a four-terminal method. The results are shown in Table 1.

TABLE 1

|  | Metal particle | Amount of $Al_2O_3$ added (wt %) | Resistance value (mΩ/□/10 µm) |
| --- | --- | --- | --- |
| Example 1 | Pt | 1 | 11.05 |
| Example 2 | (20 nm) | 10 | 23.41 |
| Example 3 | Pt—25% Pd | 1 | 25.15 |
| Example 4 | (20 nm) | 10 | 52.34 |
| Example 5 | Pt—25% Pd | 1 | 32.24 |
| Example 6 | (200 nm) | 10 | 57.10 |
| Conventional Example 1 | Pt | 1 | 19.93 |
| Conventional Example 2 |  | 10 | 37.3 |
| Conventional Example 3 | Pt—25% Pd | 1 | 41.16 |
| Conventional Example 4 |  | 10 | 65.67 |
| Comparative Example 1 | Pt | 1 | —*1 |
| Comparative Example 2 |  | 10 | ∞*2 |
| Comparative Example 3 | Pt—25% Pd | 1 | —*1 |
| Comparative Example 4 |  | 10 | ∞*2 |

*1 Unmeasurable because a film was not formed due to excessive sintering
*2 Unmeasurable because of a too high resistance value From the Table, the decrease in the resistance value was observed for the electrode prepared by the metal paste in which the conductive particle of a core/shell structure according to each of Examples was applied, and a reduction in resistance value by about 20 to 40% has been confirmed as comparison with Conventional Examples in terms of the same metal for the metal paste. The lowering of the resistance of the electrode film leads to a capability to exert a comparable performance even when the electrode film is thinner than the conventional one, and as a result it is possible to realize a reduction in the amount of the metal paste used, that is, a reduction in the amount of a precious metal used.

In addition, it has been confirmed from the results of Comparative Examples that the effect of the present invention is not exerted only by simply refining a metal particle. That is, a powder only made of Pt or a Pt—Pd alloy cannot be formed into an electrode film without a ceramic being blended, and the resistance value of an electrode becomes remarkably high even if a ceramic is mixed. The reason for ineffectiveness only by refining a conductive particle is considered as follows: a refined conductive particle easily aggregates to contrarily lower a starting temperature of sintering, and thus while an electrode film is hardly formed by mixing a small amount of a ceramic (Comparative Examples 1 and 3), a dispersion state of a ceramic particle is not improved even if an amount of a ceramic added is increased, thereby raising a resistance value.

Figure 2A:
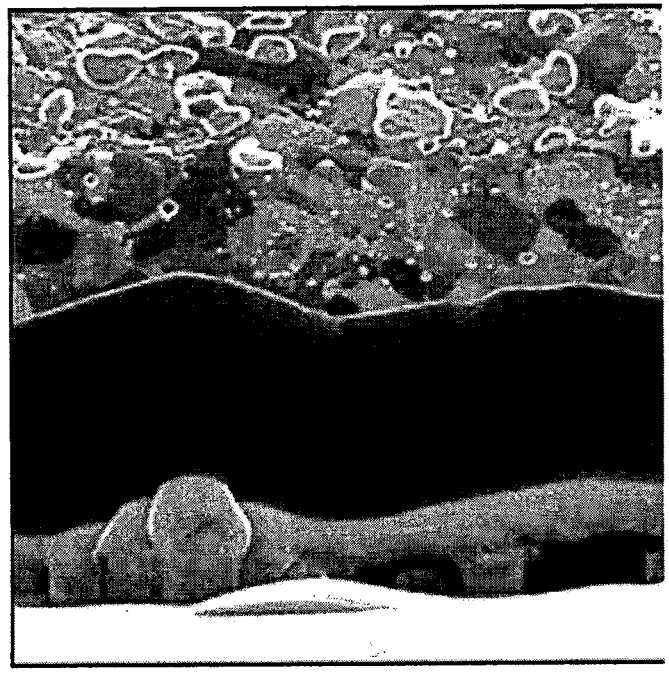
Figure 2A:
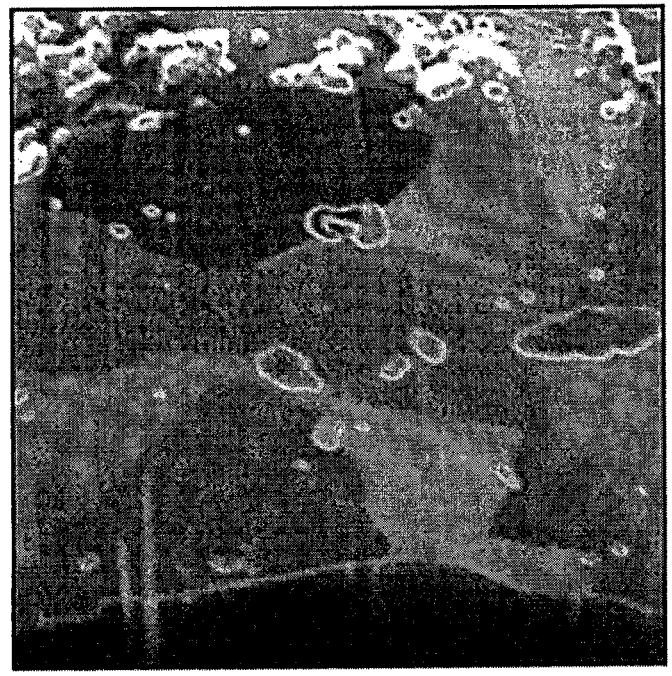

FIG. 2 shows cross-sectional photographs of electrodes produced in Example 1 and Conventional Example 1. It can be seen from FIG. 2 that an $Al_2O_3$ particle is fine and dispersed uniformly in the electrode produced in the Example. On the other hand, in the Conventional Example, it is confirmed that there is a coarse ceramic particle.

Then, characteristic of the metal paste was evaluated depending on an amount of $Al_2O_3$ added. As in Examples 1 and 2, a $Pt/Al_2O_3$ mixed powder adjusted for an amount of an $Al_2O_3$ powder mixed was released in a plasma gas phase to produce a conductive particle powder to prepare a metal paste, thereby producing an electrode film. Then, the resistance value was measured as in Examples 1 and 2. The results are shown in Table 2.

TABLE 2

| Amount of $Al_2O_3$ added (wt %) | Resistance value (mΩ/□10 μm) |
| --- | --- |
| 1% | 11.05 |
| 5% | 16.98 |
| 10% | 23.41 |
| 13% | 28.03 |
| 15% | 81.02 |
| 20% | ∞*[1] |

*[1]Unmeasurable because of too high a resistance value

The amount of $Al_2O_3$ added does not have any great adverse influence on the resistance value until it reaches 13% by weight. Although the resistance value was measurable until the amount added reached up to 15% by weight, the resistance value was unmeasurable once it exceeded 15% by weight. Therefore, it can be said that the upper limit of the amount of $Al_2O_3$ added is preferably 15% by weight.

A range of a Pd concentration was also examined when a Pt—Pd alloy was applied as a core particle. This examination was conducted as follows: 0.5 g of a Pt—Pd alloy powder having a different Pd concentration was prepared, placed on a ceramic substrate, heated to a melting point or more and melted, and a wetting angle of the resultant was measured. The results are shown in Table 3.

TABLE 3

| Amount of Pd added (wt %) | Wetting angle (°) |
| --- | --- |
| 0 | 129.0 |
| 5 | 124.6 |

TABLE 3-continued

| Amount of Pd added (wt %) | Wetting angle (°) |
| --- | --- |
| 10 | 124.2 |
| 20 | 123.6 |
| 30 | 120.9 |

It is recognizable from Table 3 that a Pt—Pd alloy has a smaller wetting angle than Pt, and more favorable compatibility to a ceramic than Pt. This behavior is considered to be effective also in a case of pasting a powder, and the lowering of the wetting angle to a substrate exhibits compatibility and coatability of a metal paste to a substrate, thereby leading to improved adhesion of an electrode. It is recognizable that an increase in the amount of Pd tends to decrease the wetting angle. Therefore, when a Pt—Pd alloy is applied to the present invention, it is sufficient to increase the content of Pd, but if the content of Pd exceeds 30% by weight as described above, a Pd oxide tends to be deposited, thereby causing the reliability of an electrode to be degraded.

Second Embodiment: A conductive particle of a core/shell structure according to the first embodiment, where $ZrO_2$ (YSZ) was applied as a shell, was here produced. With respect to the production method, the same conditions as in the first embodiment were essentially applied, and mixed powders of a Pt powder and a $ZrO_2$ (YSZ) powder was released in a plasma gas phase to produce a conductive particle of a core/shell structure. Then, a metal paste was produced as in the first embodiment, coated and calcined on a zirconia substrate to form an electrode film, and the resistance value of the electrode film was measured. In addition, for comparison, characteristic of an electrode film of a metal paste obtained by mixing a Pt powder and a $ZrO_2$ (YSZ) powder separately was also evaluated. The results are shown in Table 4.

TABLE 4

| | Metal particle | Amount of $ZrO_2$ added (wt %) | Resistance value (mΩ/□10 μm) |
| --- | --- | --- | --- |
| Example 7 | Pt | 1 | 10.99 |
| Example 8 | | 10 | 22.20 |
| Conventional Example 5 | Pt | 1 | 14.91 |
| Conventional Example 6 | | 10 | 30.85 |

As can be seen from the Table, it was observed that the resistance of the conductive particle with $ZrO_2$ (YSZ) as a shell decreased compared to the metal paste of each of the Conventional Examples.

Third Embodiment: An examination was conducted for clarifying the lower limit of an amount of a ceramic (shell) covering a conductive particle of a core/shell structure. The conductive particle of a core/shell structure was produced as in First Embodiment by releasing mixed powders of a Pt powder and an $Al_2O_3$ powder in a plasma gas phase. The amount in which the shell is covered was set by adjusting an amount of the $Al_2O_3$ powder in the mixed powders. Then, a metal paste was produced as in the first embodiment, coated and calcined on an alumina substrate in three kinds of patterns, 0.5×20 mm (three lines at intervals of 1 mm), 0.1×5.0 mm (eleven lines at intervals of 0.1 to 0.5 mm), and 5×5 mm. After calcining, the presence or absence of peeling and warpage of an electrode film was confirmed. The results are shown in Table 5.

TABLE 5

| Amount of Al₂O₃ added | Warpage | Peeling |
|---|---|---|
| 3 wt % | ◉ | ◉ |
| 1 wt % | ◉ | ◉ |
| 0.7 wt % | ◉ | ◉ |
| 0.5 wt % | ○ | ◉ |
| 0.4 wt % | X | ○ |
| 0.3 wt % | X | X |

◉ . . . There is no warpage/peeling.
○ . . . There is hardly any warpage/peeling, but partially arises.
X . . . There is clearly warpage/peeling.

It is recognizable from Table 5 that when the amount of a ceramic is low, peeling or deformation is likely to occur after calcining. Then, it can be confirmed that the lower limit of a practically acceptable amount of a ceramic is 0.5% by weight. It is to be noted that while the results are obtained in a case of applying $Al_2O_3$ as a ceramic, the similar results are also obtained in a case of using $ZrO_2$.

INDUSTRIAL APPLICABILITY

According to the present invention, a metal paste for electrode formation that can produce an electrode having a low resistance can be provided.

What is claimed is:

1. A metal paste for sensor electrode formation consisting of a conductive particle having a core/shell structure, a solvent, and one or more resins selected from the group consisting of a natural resin, an amino-based resin, and an alkyd resin, wherein said conductive particle comprises:
a core particle that is made of Pt or a Pt alloy and has a particle diameter of 10 to 200 nm;
and a shell that is made of a ceramic comprising $Al_2O_3$ or $ZrO_2$ and covers at least a part of the core particle, and wherein the ceramic constituting the shell is present in an amount of 0.5 to 15% by weight based on the core particle to cover the core.

2. The metal paste according to claim 1, wherein the core particle is Pt.

3. The metal paste according to claim 2, wherein the core particle is Pt or a Pt alloy further comprising 3% by weight or less of Al or Zr.

4. The metal paste according to claim 1, wherein the core particle is a Pt-Pd alloy comprising 30% by weight or less of Pd.

5. The metal paste according to claim 4, wherein the core particle is Pt or a Pt alloy further comprising 3% by weight or less of Al or Zr.

6. The metal paste according to claim 1, wherein the core particle is Pt or a Pt alloy further comprising 3% by weight or less of Al or Zr.

7. The metal paste according to claim 1, wherein the solvent is selected from the group consisting of one or more of ethylene glycol, propylene glycol, ethyl cellosolve, butyl cellosolve, ethylene glycol monophenyl ether, ethylene glycol monomethyl ether acetate, benzyl alcohol, kerosene, paraffin, toluene, cyclohexanone, γ-butyrolactone, methyl ethyl ketone, N-methyl pyrrolidone, N-dimethyl formamide, N-methyl acetamide, N.N-dimethyl acetamide, butyl carbitol, turpentine oil, α-terpineol, and terpineol.

* * * * *